United States Patent
Ueno et al.

(10) Patent No.: US 8,171,796 B2
(45) Date of Patent: May 8, 2012

(54) ACOUSTIC EMISSION DETECTOR AND CONTROLLER

(75) Inventors: Hiroshi Ueno, Tondabayashi (JP); Kazutoshi Toda, Tondabayashi (JP); Kazuya Suzuki, Kashiwara (JP); Satoshi Hashimoto, Kyoto (JP); Alexei Vinogradov, Osaka (JP)

(73) Assignees: JTEKT Corporation, Osaka (JP); Satoshi Hashimoto, Kyoto (JP); Alexei Vinogradov, Osaka (JP)

( * ) Notice: Subject to any disclaimer, the term of this patent is extended or adjusted under 35 U.S.C. 154(b) by 407 days.

(21) Appl. No.: 12/301,347

(22) PCT Filed: May 24, 2007

(86) PCT No.: PCT/JP2007/060607
§ 371 (c)(1),
(2), (4) Date: Jul. 14, 2009

(87) PCT Pub. No.: WO2007/136111
PCT Pub. Date: Nov. 29, 2007

(65) Prior Publication Data
US 2010/0058867 A1    Mar. 11, 2010

(30) Foreign Application Priority Data
May 24, 2006 (JP) .................................. 2006-144248

(51) Int. Cl.
G01N 29/14 (2006.01)
G06F 19/00 (2011.01)
(52) U.S. Cl. ............................................ 73/587; 702/56

(58) Field of Classification Search ............... 73/587, 73/593, 599, 600, 602, 645; 702/56
See application file for complete search history.

(56) References Cited

U.S. PATENT DOCUMENTS

| | | | | |
|---|---|---|---|---|
| 5,140,858 A * | 8/1992 | Nishimoto et al. | ............. | 73/587 |
| 6,339,961 B1 * | 1/2002 | Goodman et al. | ............. | 73/593 |
| 6,370,957 B1 * | 4/2002 | Filippenko et al. | ............. | 73/660 |
| 6,415,189 B1 * | 7/2002 | Hajji | ............. | 700/79 |
| 6,418,384 B1 * | 7/2002 | Rothea et al. | ............. | 702/56 |
| 7,182,519 B2 * | 2/2007 | Singh et al. | ............. | 384/448 |
| 7,370,537 B2 * | 5/2008 | O'Brien et al. | ............. | 73/818 |
| 7,435,004 B2 * | 10/2008 | Singh et al. | ............. | 384/448 |

FOREIGN PATENT DOCUMENTS

| JP | 4-268450 | 9/1992 |
|---|---|---|
| JP | 7-43352 | 2/1995 |

(Continued)

OTHER PUBLICATIONS

English translation of the International Preliminary Report on Patentability mailed Dec. 24, 2008 in corresponding PCT Application No. PCT/JP2007/060607.

(Continued)

*Primary Examiner* — Jacques M Saint Surin
(74) *Attorney, Agent, or Firm* — Nixon & Vanderhye P.C.

(57) ABSTRACT

An AE detector has an AE sensor and a destruction judging section. The destruction judging section judges it as a warning of destruction of a bearing when there are a predetermined number or more of points defined by parameters calculated based on signals from the AE sensor in a predetermined region of a parameter space defined by a plurality of parameters which can be created based on the signals from the AE sensor.

4 Claims, 8 Drawing Sheets

FOREIGN PATENT DOCUMENTS

| | | |
|---|---|---|
| JP | 7-168619 | 7/1995 |
| JP | 7-318457 | 12/1995 |
| JP | 2001-324417 | 11/2001 |
| JP | 2003-98162 | 4/2003 |
| JP | 2004-61202 | 2/2004 |
| JP | 2004-301017 | 10/2004 |

OTHER PUBLICATIONS

International Search Report for PCT/JP2007/060607, mailed Aug. 7, 2007.

* cited by examiner

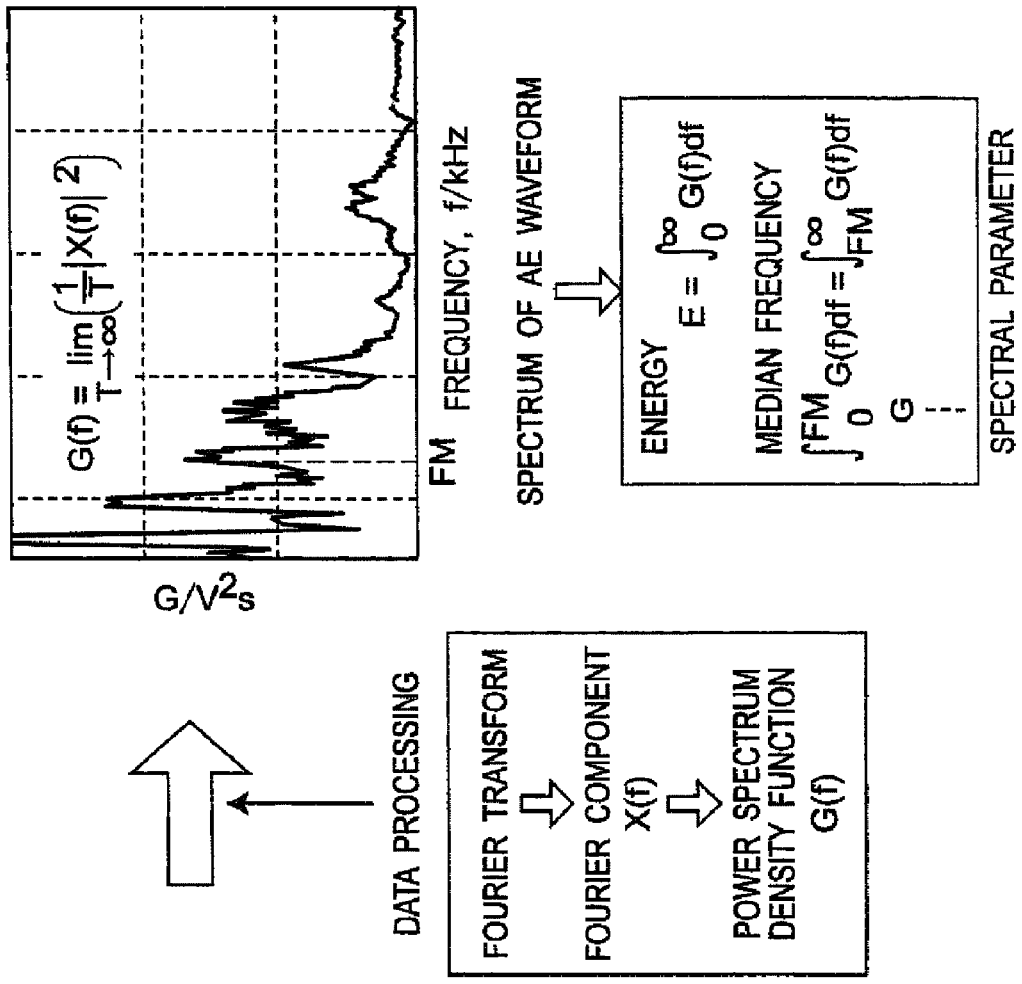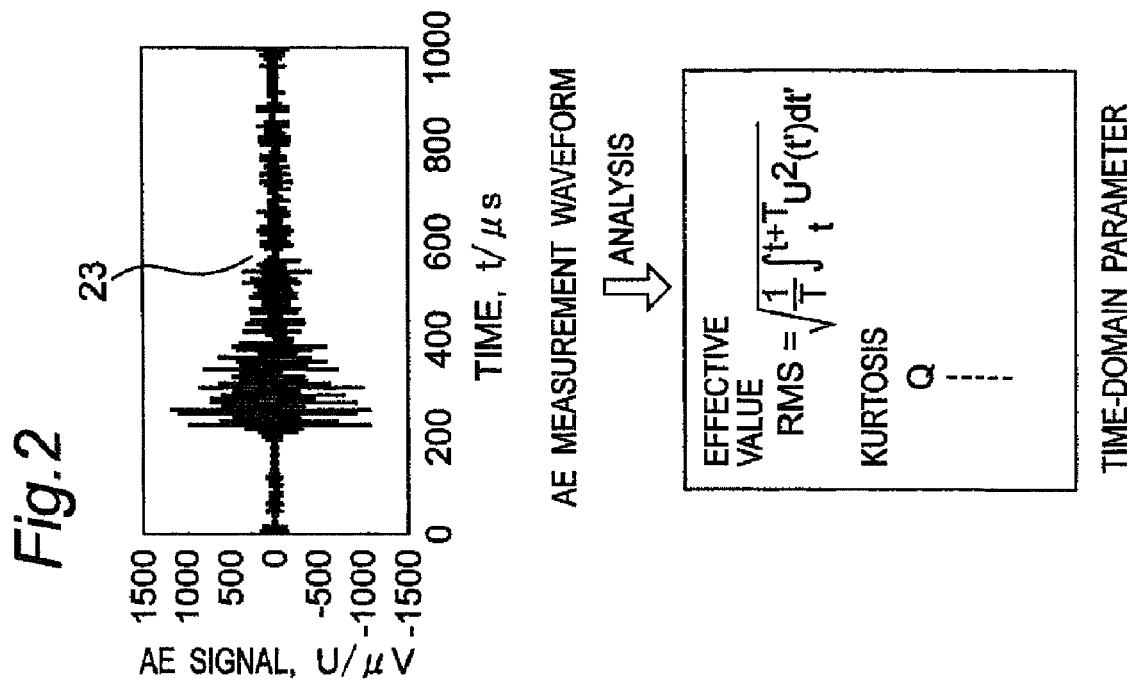
Fig.2

ACOUSTIC EMISSION DETECTOR AND CONTROLLER

This application is the U.S. national phase of International Application No. PCT/JP2007/060607, filed 24 May 2007, which designated the U.S. and claims priority to Japan Application No. 2006-144248, filed 24 May 2006, the entire contents of each of which are hereby incorporated by reference.

TECHNICAL FIELD

The present invention relates to an acoustic emission detector and a controller that has the acoustic emission detector.

BACKGROUND ART

Conventionally, an AE (Acoustic Emission) detector that detects a warning of destruction by acoustic emission is described in JP 7-318457 A.

Moreover, another conventional AE detector measures the amplitude of AE generated in a machine to which the AE detector is attached and judges it as a warning of destruction when the amplitude becomes greater than a predetermined value.

However, the AE detector, which judges the warning of destruction simply by the amplitude of AE, sometimes misjudges a mere noise as a warning of destruction, posing a problem that certainty and reliability are low.

SUMMARY OF THE INVENTION

An object of the present invention is to provide an acoustic emission detector that is able to accurately detect a warning of destruction and has high reliability and a controller that has the acoustic emission detector.

In order to solve the above problem, an acoustic emission detector of the invention comprises:

an acoustic emission sensor to detect an acoustic emission; and a destruction judging section that judges it as a warning of destruction of a material subject to destruction detection when a predetermined number or more of points defined by at least two parameters calculated based on a signal from the acoustic emission sensor are located within a predetermined region of a parameter space in the parameter space defined by at least two parameters that can be generated based on the signal from the acoustic emission sensor.

As described in detail hereinafter, the inventors discovered the fact that, when a parameter space defined by at least two parameters was appropriately selected, the points defined by the at least two parameters calculated based on the signal from the acoustic emission sensor in the parameter space were located within the first predetermined region of the parameter space when there was no warning of destruction of the material subject to destruction detection and the fact that the points were located within the second predetermined region other than the first predetermined region of the parameter space when there was a warning of destruction of the material subject to destruction detection. Moreover, the inventors discovered the fact that, when the destruction of the material subject to destruction detection occurred, a large majority of points were located within a third region different from the first and second predetermined regions in the parameter space. Moreover, the inventors discovered the fact that, upon judging the warning of destruction of the material subject to destruction detection by using the above fact, the influence of noises could be eliminated in comparison with the conventional case, and the warning of destruction of the material subject to destruction detection could be judged remarkably rapidly and accurately.

According to the invention, it is judged as a warning of destruction of the material subject to destruction detection when the predetermined number or more of points defined by the at least two parameters calculated based on the signal from the acoustic emission sensor are located within the predetermined region of the parameter space. Therefore, the warning of destruction can be accurately detected, and the warning of destruction of the material subject to destruction detection can be judged promptly with high reliability.

In one embodiment, the parameter space comprises:

a first parameter space defined by at least two parameters; and a second parameter space that is defined by at least two parameters and is different from the first parameter space.

According to the above embodiment, there are two parameter spaces to judge the warning of destruction of the material subject to destruction detection, and therefore, the warning of destruction of the material subject to destruction detection is not misjudged.

One embodiment comprises:

a calculating section that calculates a plurality of parameters based on the signal outputted from the acoustic emission sensor; and a correlation parameter determining section that determines mutually correlated parameters among the plurality of parameters, wherein the destruction judging section judges it as a warning of destruction of the material subject to destruction detection when a predetermined number or more of points defined by mutually correlated parameters calculated based on the signal from the acoustic emission sensor are located within a predetermined region of the parameter space defined by the mutually correlated parameters in the parameter space defined by the mutually correlated parameters determined by the correlation parameter determining section.

According to the above embodiment, the correlation parameter determining section to determine the correlated parameters is provided. Therefore, a warning of destruction can be correctly judged not only in the case of a material subject to destruction detection of which the mutually correlated parameters can be generated based on the signal from the acoustic emission and of which the mutually correlated parameters have previously been known, but also even in the case of a material subject to destruction detection of which the mutually correlated parameters can be generated based on the signal from the acoustic emission and of which the mutually correlated parameters have not previously been known.

In one embodiment, the at least two parameters are two or more parameters of UP, RMS, FC, $G_{max}$, E, FM, WEFF and Q.

In the present specification, the UP is a peak value of an acoustic emission voltage signal.

Moreover, the RMS is the effective value. When a certain specified time width T is determined and an acoustic emission waveform is further expressed by a voltage signal that is a function of time and based on the output of the acoustic emission sensor, the RMS is a value obtained by integrating the square of the amplitude of the voltage signal over a period T from a definite time point to a time point subsequent to the definite time point, dividing the resultant by T and thereafter further taking the root of the value obtained through the division by T.

Moreover, a power spectrum density function G(f) is obtained by obtaining a power spectrum by subjecting an acoustic emission waveform expressed by time and a voltage signal based on the output of the acoustic emission sensor to Fourier transform and squaring the resultant and further dividing the same by frequency decomposition.

Moreover, the FC is a center frequency. the FC is a frequency that represents a peak by the power spectrum density function G(f).

Moreover, the $G_{max}$ is a maximum value of a power spectrum. The $G_{max}$ is a peak level in the power spectrum density function G(f).

Moreover, the E is energy. The E is a value obtained by integrating the power spectrum density function G(f) of a function of frequency f from frequency zero to infinity.

Moreover, the FM is a median frequency. The FM is a frequency determined by the fact that a value obtained by integrating the power spectrum density function G(f) from zero to the FM is equal to a value obtained by integrating the power spectrum density function G(f) from the FM to infinity.

Moreover, the WEFF means an effective width. The WEFF is a frequency determined by, assuming that the level of the power spectrum maximum value $G_{max}$ is rectangularly distributed from frequency zero to the frequency WEFF in the power spectrum density function, the fact that its energy is equal to the actual energy E described above.

Moreover, the Q is kurtosis (degree of peakedness) of the acoustic emission waveform. The Q is defined by the following equation. In the following equation, N is the number of events, $U_j$ is an acoustic emission voltage value, and $\sigma_U$ is the standard deviation of $U_j$. Moreover, $\overline{U}$ is the mean value of $U_j$.

$$Q = \frac{1}{N} \sum_{j=1}^{N} \left[ \frac{U_j - \overline{U}}{\sigma_u} \right]^4 - 3$$

According to the above embodiment, the at least two parameters are two or more parameters among the UP, RMS, FC, $G_{max}$, E, FM, WEFF and Q. Therefore, the at least two parameters can easily be calculated based on the signal of the acoustic emission sensor.

Moreover, a controller of the invention comprises:

the acoustic emission detector; and a neural network that receives at least an output of the acoustic emission detector and outputs a control signal.

The controller of the invention may receive signals from a plurality of the acoustic emission detectors of the invention. Moreover, the controller of the invention may further receive an output of a device other than the acoustic emission detector of the invention.

According to the above invention, the neural network receives the output of the acoustic emission detector and outputs the control signal. Therefore, the neural network can be made to lean the relation between the parameters and the presence or absence of a warning of destruction, and the result of learning can be reflected on the control signal. Therefore, a more prompt and accurate control signal can be outputted as the neural network is used more and more.

According to the acoustic emission detector of the invention, it is judged as a warning of destruction of a material subject to destruction detection when a predetermined number or more of points defined by at least two parameters calculated based on a signal from an acoustic emission sensor are located within a predetermined region of a parameter space. Therefore, only a warning of destruction can reliably be detected, and a warning of destruction of the material subject to destruction detection can be judged promptly with high reliability.

BRIEF DESCRIPTION OF THE DRAWINGS

FIG. 2 is a diagram for explaining a process through which various parameters are calculated from an AE measurement waveform;

DETAILED DESCRIPTION OF THE INVENTION

Figure 1:
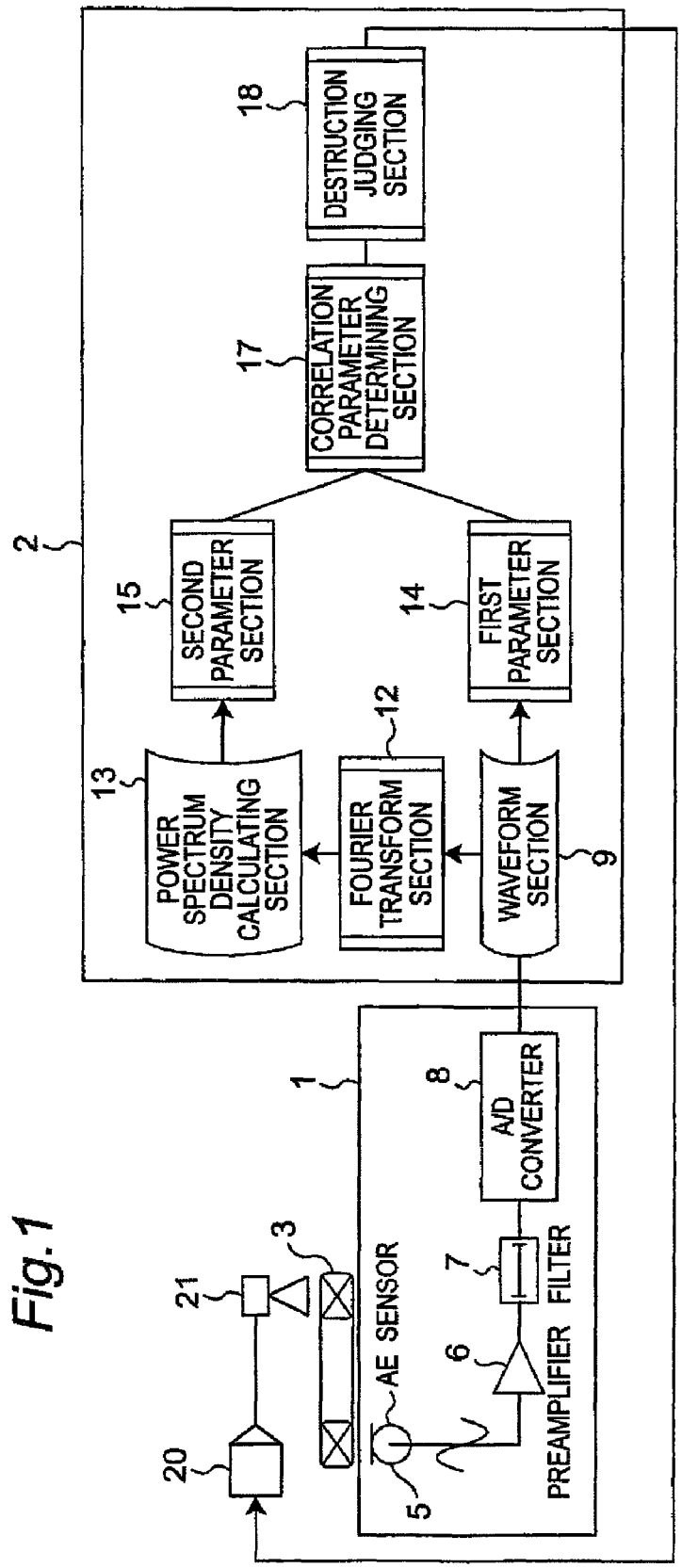
FIG. 1 is a diagram showing the construction of an AE detector according to a first embodiment of the invention.

The invention will be described in detail below by the embodiments shown in the drawings.

FIG. 1 is a diagram showing the construction of an acoustic emission detector (hereinafter referred to as an AE detector) according to the first embodiment of the invention.

The AE detector of the invention calculates various parameters by obtaining acoustic emission (hereinafter referred to as AE) data and performing processing of Fourier transform or the like. Moreover, the AE detector of the invention judges the presence or absence of a warning of destruction of a bearing 3 and the destruction of the bearing 3 as one example of material subject to destruction detection by calculating the various parameters and thereafter carrying out a factor analysis by correlation calculation between the parameters and a cluster analysis utilizing it.

In detail, the AE detector has an AE obtaining part 1 and a signal analyzing part 2. The AE obtaining part 1 has an acoustic emission sensor (hereinafter referred to as an AE sensor) 5 installed on the bearing 3, a preamplifier 6 connected to the output side of the AE sensor 5, a filter 7 connected to the output side of the preamplifier 6, and an A/D converter 8 connected to the output side of the filter 7. A signal from the AE sensor 5 is amplified by the preamplifier 6 and thereafter put through the filter 7 to cut off a frequency domain where only noises exist in the signal amplified by the preamplifier 6. Subsequently, an analog signal, of which the frequency domain where only noises exist has been cut off, is converted into a digital signal by the A/D converter 8.

The digital signal from the A/D converter 8 is inputted to the signal analyzing part 2. The signal analyzing part 2 has a waveform section 9, a Fourier transform section 12, a power spectrum density calculating section 13, a first parameter section 14, a second parameter section 15, a correlation parameter determining section 17 and a destruction judging section 18.

The waveform section 9 receives the digital signal from the A/D converter 8 and displays the relation between time and the digital signal. The Fourier transform section 12 receives the signal from the waveform section 9 and subjects the waveform displayed by the waveform section 9 to Fourier transform. The power spectrum density calculating section 13 calculates a power spectrum density function by using a Fourier component calculated by carrying out the Fourier transform by the Fourier transform section 12.

The first parameter section 14 calculates various time-domain parameters based on the signal from the waveform section 9. The second parameter section 15 calculates various spectral parameters based on the signal from the power spectrum density calculating section 13.

The correlation parameter determining section 17 receives the signal from the first parameter section 14 and the signal from the second parameter section 15 and carries out a factor analysis. The destruction judging section 18 receives the signal from the correlation parameter determining section 17 and carries out a cluster analysis to output the presence or absence of the warning of destruction of the bearing 3 or the destruction of the bearing 3. The destruction judging section 18 outputs a signal to a lubrication mechanism.

The lubrication mechanism is constructed of a pump controller 20 and a pump 21. The pump controller 20 outputs a signal that represents supply of lubricant to the bearing 3 to the pump 21 upon receiving the signal representing that a warning of destruction is observed in the bearing 3 from the destruction judging section 18. Moreover, the pump 21 supplies the lubricant to the bearing 3 upon receiving the signal that represents supply of the lubricant to the bearing 3. The first parameter section 14 and the second parameter section 15 constitute a calculating section.

The first parameter section 14 calculates UP, RMS and Q that are time-domain parameters based on the waveform from the waveform section 9, or in detail, a waveform that represents the relation between time and the digital amplitude of AE. Moreover, the second parameter section 15 calculates E (energy), FM (median frequency), FC, $G_{max}$ and WEFF that are spectral parameters based on the power spectrum density function from the power spectrum density calculating section 13.

FIG. 2 is a diagram for explaining a process through which various parameters are calculated from an AE measurement waveform.

A waveform section (indicated by numeral 9 in FIG. 1) that has received the signal from the AD converter (indicated by numeral 8 in FIG. 1) forms, for example, the AE measurement waveform indicated by numeral 23 and outputs a signal that represents the AE measurement waveform 23 to the Fourier transform section (indicated by numeral 12 in FIG. 1) and the first parameter section (indicated by numeral 14 in FIG. 1). Then, the first parameter section analyzes the AE measurement waveform that is a function of time and calculates time-domain parameters such as RMS (effective value), Q (kurtosis) and so on based on the AE measurement waveform. These are calculated every predetermined time based on the AE measurement waveform in a predetermined duration.

On the other hand, the Fourier transform section, which has received the signal that represents the AE measurement waveform 23 from the waveform section 9, subjects the AE measurement waveform to Fourier transform to calculate a Fourier component X(f) that is a function of frequency. Moreover, the power spectrum density calculating section (indicated by numeral 13 in FIG. 1), which has received the signal from the Fourier transform section, calculates a power spectrum density function G(f) by using the Fourier component X(f). Moreover, the second parameter section (indicated by numeral 15 in FIG. 1), which has received the signal from the power spectrum density calculating section 13, calculates the spectral parameters of E (energy), FM (median frequency) and so on by using the power spectrum density function G(f).

Figure 3:
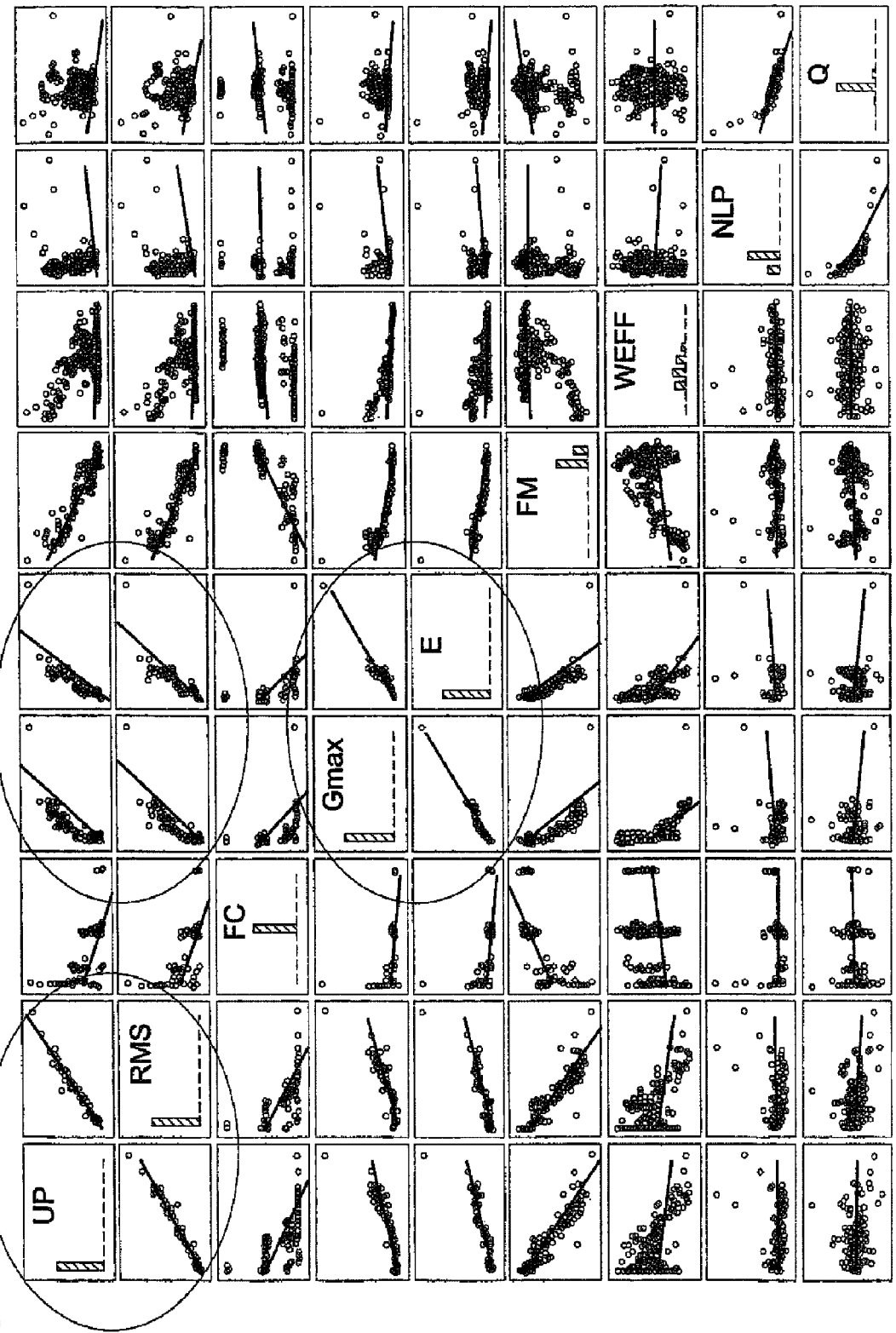
FIG. 3 is a diagram showing a result of factor analysis of a correlation parameter determining section.

FIG. 3 is a diagram showing a result of factor analysis of the correlation parameter determining section (indicated by numeral 17 in FIG. 1).

The correlation parameter determining section (indicated by numeral 17 in FIG. 1) receives signals from the first parameter section (indicated by numeral 14 in FIG. 1) and the second parameter section (indicated by numeral 15 in FIG. 1) and performs a factor analysis. In detail, as shown in FIG. 3, the correlation parameter determining section calculates all two-dimensional correlations of all combinations of the parameters UP, RMS, FC, $G_{max}$, E, FM, WEFF and Q calculated by the calculating sections (first parameter section and second parameter section). Then, mutually correlated parameters among the plurality of parameters are determined.

In concrete, correlation coefficients of the combinations are calculated, and parameter combinations of which the absolute value of the correlation coefficient is not smaller than a predetermined value (e.g., not smaller than 0.80) and which have a strong tendency of linearity are picked up. For example, in the example shown in FIG. 3, parameter combinations, which have a strong tendency of linearity and of which the absolute value of the correlation coefficient is large, exist in the combination of UP and RMS, the combination of $G_{max}$ and E and so on. The correlation parameter determining section picks up the combinations that have a strong tendency of linearity.

The inventors discovered the fact that, in a parameter space constituted of a plurality of parameters that had exhibited a strong correlation through the factor analysis of all the correlations, points defined by the plurality of parameters calculated based on the signal from the AE sensor were located within a first predetermined region of the parameter space when there was no warning of destruction of the material subject to destruction detection and the fact that the points were located within a second predetermined region other than the first predetermined region of the parameter space when there was a warning of destruction of the material subject to destruction detection.

Moreover, the inventors discovered the fact that a large majority of points were located within a third region different from the first predetermined region and the second predetermined region of the parameter space when the destruction of the material subject to destruction detection occurred. Moreover, the inventors discovered the fact that the influence of noises can be removed and the warning of destruction of the material subject to destruction detection can be judged more rapidly and accurately than in the conventional case if the above fact is utilized. The fact is described below.

Upon receiving the signal from the correlation parameter determining section, the destruction judging section (indicated by numeral 18 in FIG. 1) performs a scatter analysis. In detail, the destruction judging section judges it as a warning of destruction of the bearing (indicated by numeral 3 in FIG. 1) when a predetermined number or more of points defined by the correlated parameters calculated based on the signal from the AE sensor exist in a predetermined region of the parameter space defined by the correlated parameters in the parameter space defined by the correlated parameters determined by the correlation parameter determining section. The fact is described in detail below with reference to FIG. 4.

Figure 4:
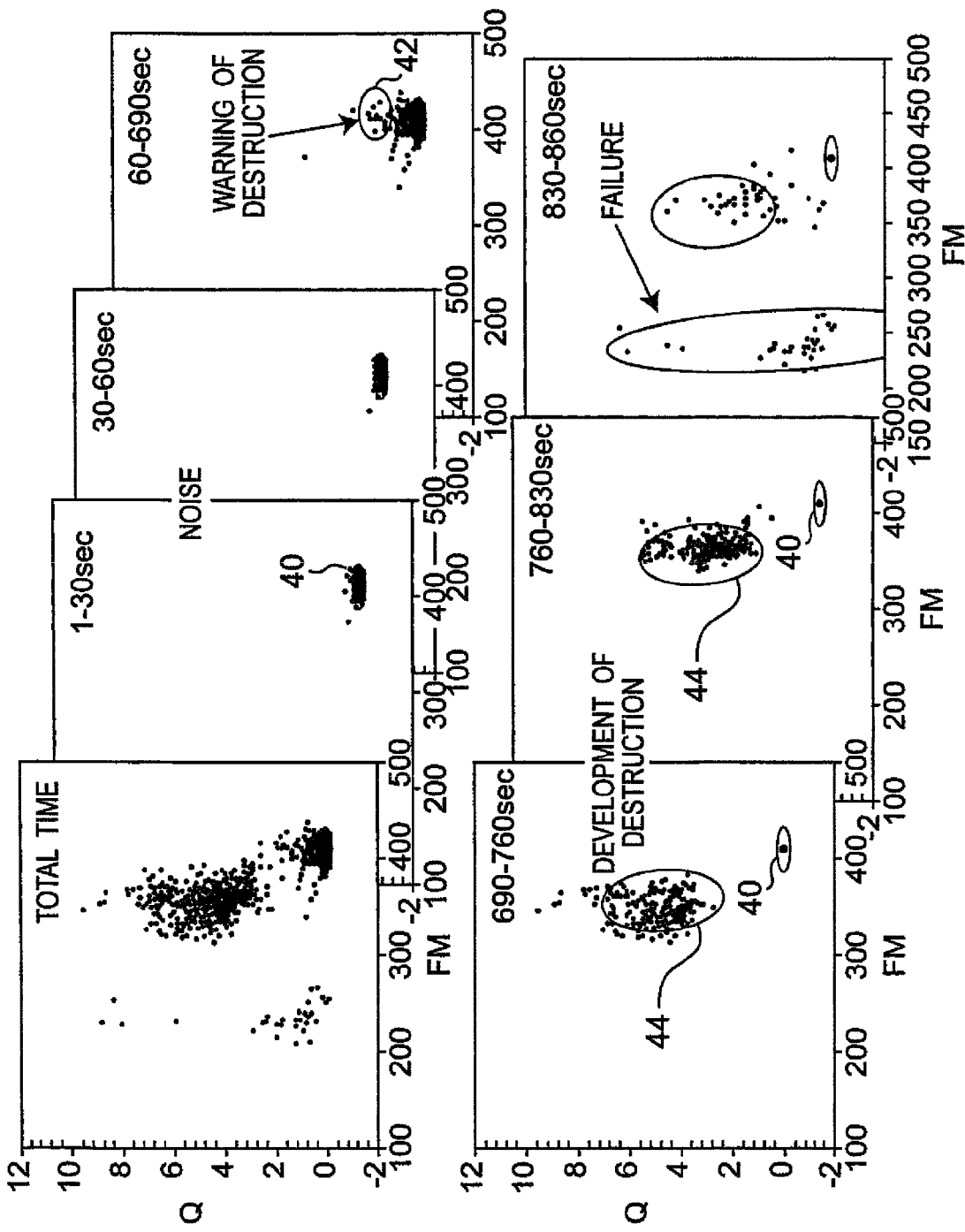
FIG. 4 is a diagram for explaining a signal analysis of a destruction judging section and a method for judging a warning of destruction in one experimental example.

FIG. 4 is a diagram for explaining a signal analysis of a destruction judging section and a method for judging a warning of destruction in one experimental example. FIG. 4 shows the results of a scatter analysis in stages at different levels of destruction. In FIG. 4, FM (median frequency) and Q (kurtosis), which are correlated, are two parameters that exhibit a strong correlation and are picked up by the correlation parameter determining section with regard to a bearing that is one example of the material subject to destruction detection.

As shown in FIG. 4, in the correlation diagram of FM and Q, points defined by FM and Q calculated based on the signal from the AE sensor are located generally within the first region 40 of the parameter space defined by FM and Q in the initial duration of 30 seconds (1 to 30 seconds) of the signal outputted from the AE sensor with a starting point set at a definite time. In this case, utterly no warning of destruction of the bearing was observed. This indicates that these points are presumably based on noises in the peripheries of the bearing. Moreover, in the next duration of 30 seconds (30 seconds to 60 seconds), points defined by FM and Q calculated based on the signal from the AE sensor are also generally located within the first region 40. Also, at this time, no warning of destruction was observed in the first region 40.

Subsequently, in a duration of 60 seconds to 690 seconds, points defined by FM and Q calculated based on the signal from the AE sensor are located in the peripheral region of the first region 40 and spread to a second region 42 as a predetermined region that does not intersect with the first region. Then, five, as one example of the predetermined number, or more points defined by FM and Q are located within the second region 42. The AE detector of the first embodiment determines a warning of destruction of the bearing at this time. Moreover, a warning of destruction was actually observed in the bearing at this time. Subsequently, in a duration of 690 seconds to 760 seconds, points defined by FM and Q calculated based on the signal from the AE sensor are located within a different third region 44 apart from the first region 42. At this time, the destruction of the bearing has progressed. Subsequently, also in a duration of 760 seconds to 830 seconds, points defined by FM and Q calculated based on the signal from the AE sensor are located within the third region 44 apart from the first region 40. Also, at this time, the progress of the destruction of the bearing was confirmed. Lastly, in a duration of 830 seconds to 860 seconds, points defined by FM and Q calculated based on the signal from the AE sensor are scattered on the parameter space. At this time, the destruction of the bearing was observed.

It is noted that a vibrometer installed concurrently with the AE sensor on the bearing detected the destruction of the bearing at this timing, i.e., in the duration of 830 seconds to 860 seconds. As described above, the AE detector of the present embodiment is able to measure not the destruction of the bearing that is the material subject to destruction detection but the warning of destruction of the bearing in a stage two or more minutes precedent to the vibrometer. Then, by supplying lubricant to the bearing by the lubrication mechanism at the time point when the AE detector previses a warning of destruction, failures such as the seizure of the members that constitute the bearing and the exfoliation of the raceway surface of the bearing can reliably be prevented. This tells that the bearing does not reach failure as in the conventional case if the AE detector of the present embodiment is employed. Moreover, as apparent also from the above description, the AE detector of the present embodiment adopts the system in which the noise signal is used as the normal signal. Therefore, a warning of destruction can be judged accurately and promptly without being puzzled at all by noises unlike the conventional AE detector.

Figure 5:
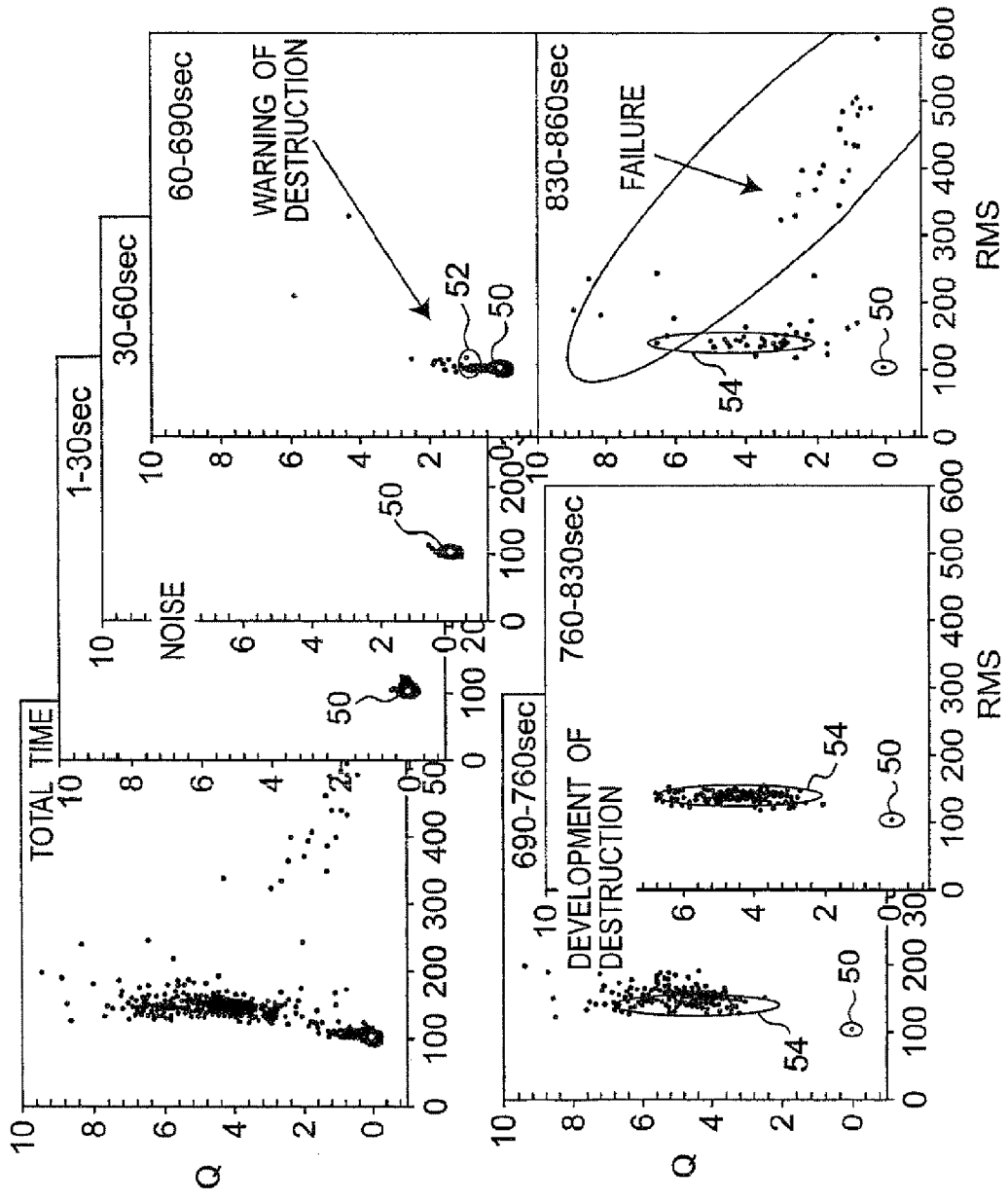
FIG. 5 is a diagram showing a signal analysis based on RMS and Q and the time of a warning of destruction in the one experimental example.

FIG. 5 is a diagram showing a signal analysis based on RMS and Q that has exhibited a strong correlation other than FM (median frequency) and Q (kurtosis) and the time of a warning of destruction in the above one experimental example.

As shown in FIG. 5, also in the analysis using RMS and Q, points defined by RMS and Q calculated based on the signal from the AE sensor are located generally within a first region 50 of a parameter space defined by RMS and Q in the initial duration of 30 seconds (one to 30 seconds), and points defined by RMS and Q calculated based on the signal from the AE sensor are also located generally within the first region 50 of the parameter space defined by RMS and Q in the next duration of 30 seconds (30 seconds to 60 seconds). Moreover, in a duration of 60 seconds to 690 seconds, points defined by RMS and Q calculated based on the signal from the AE sensor are located in the peripheral region of the first region 50 and spread to a second region 52 that does not intersect with the first region 50. At this time, five, as one example of the predetermined number, or more points defined by RMS and Q are located within the second region 52. Moreover, in a duration of 690 seconds to 760 seconds and a duration of 760 seconds to 830 seconds, points defined by RMS and Q calculated based on the signal from the AE sensor are located within a different third region 54 apart from the first region 50. Lastly, in a duration of 830 seconds to 860 seconds, it is observed that the points defined by RMS and Q calculated based on the signal from the AE sensor are scattered on the parameter space. As described above, the analysis and the judgment of a warning of destruction using RMS and Q utterly coincide with the analysis and the judgment of a warning of destruction using FM and Q.

For the above reasons, a warning of destruction can be detected accurately and promptly even if a warning of destruction of the bearing is judged by the parameter space defined by RMS and Q that exhibit a strong correlation instead of using FM and Q that exhibit a strong correlation.

Moreover, assuming that the parameter space defined by FM and Q is a first parameter space and the parameter space defined by RMS and Q is a second parameter space (space different from the first parameter space defined by FM and Q), if it is judged as a warning of destruction of the bearing when a predetermined number or more of points defined by two or more parameters calculated based on the signal from the AE sensor in the first parameter space are located within a predetermined region of the first parameter space and when a predetermined number or more of points defined by two or more parameters calculated based on the signal from the AE sensor in the second parameter space are located within a predetermined region of the second parameter space, then a warning of destruction can be judged without mistake.

Figure 6:
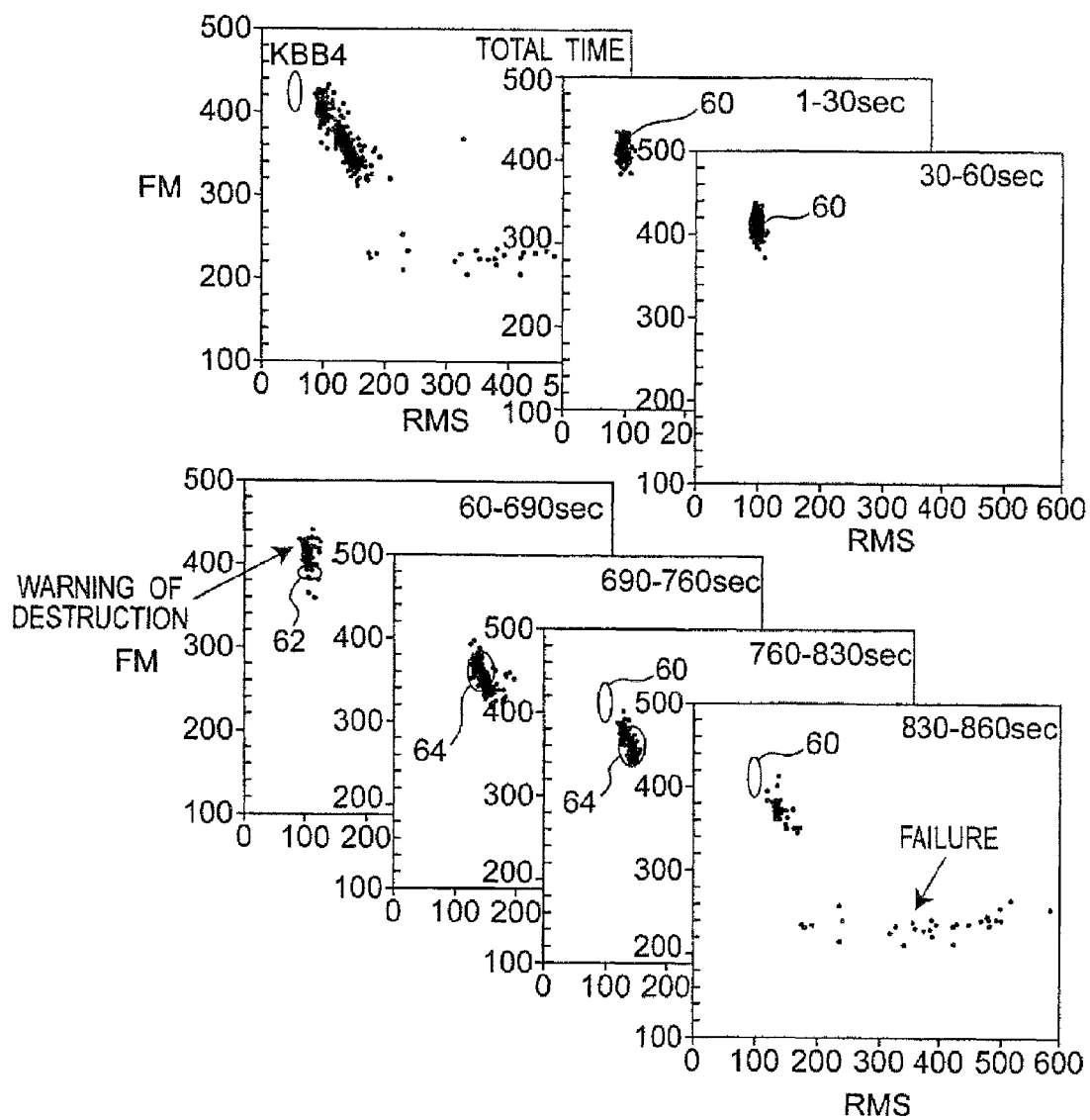
FIG. 6 is a diagram showing a signal analysis based on RMS and FM and the time of a warning of destruction in the one experimental example.

FIG. 6 is a diagram showing a signal analysis based on RMS and FM that has exhibited a strong correlation other than FM and Q and other than RMS and Q and the time of a warning of destruction in the above one experimental example.

As shown in FIG. 6, also in the analysis using RMS and FM, points defined by RMS and FM calculated based on the signal from the AE sensor are located generally within a first region 60 of a parameter space defined by RMS and FM in the initial duration of 30 seconds (one to 30 seconds), and points defined by RMS and FM calculated based on the signal from the AE sensor are also located generally within the first region 60 in the next duration of 30 seconds (30 seconds to 60 seconds). Moreover, in a duration of 60 seconds to 690 seconds, points defined by RMS and FM calculated based on the signal from the AE sensor are located in the peripheral region of the first region 60 and spread to a second region 62 that does not intersect with the first region 60. At this time, five, as one example of the predetermined number, or more points defined by RMS and FM are located within the second region 62. Moreover, in a duration of 690 seconds to 760 seconds and a duration of 760 seconds to 830 seconds, points defined by RMS and FM calculated based on the signal from the AE sensor are located within a different third region 64 apart from the first region 60. Lastly, in a duration of 830 seconds to 860 seconds, points defined by RMS and FM calculated based on the signal from the AE sensor are scattered on the parameter space. As described above, the analysis and the judgment of a warning of destruction using RMS and FM utterly coincide with the analysis and the judgment of a warning of destruction using FM and Q and the analysis and the judgment of a warning of destruction using RMS and Q.

According to the AE detector of the first embodiment, it is judged as a warning of destruction of the bearing 3 as one example of the material subject to destruction detection when a predetermined number or more (five or more in the above example) of points defined by two or more parameters (FM and Q, RMS and Q, or RMS and FM in the above example) calculated based on the signal from the AE sensor 5 are located within the second region, or the predetermined region of the parameter space defined by the two or more parameters. Therefore, a warning of destruction can reliably be detected, and a warning of destruction of the bearing 3 can be judged promptly with high reliability. Moreover, in the case of two parameter spaces (two parameter spaces among the three parameter spaces constituted of FM and Q, RMS and Q, and RMS and FM in the above example) to judge a warning of destruction of the bearing 3, a warning of destruction of the bearing 3 can be determined without mistake.

Moreover, according to the AE detector of the first embodiment, which has the correlation parameter determining section 17 to determine correlated parameters, a warning of destruction can therefore be correctly judged not only in the case of a material subject to destruction detection of which the mutually correlated parameters have previously been known, but also even in the case of a material subject to destruction detection of which the correlated parameters have not previously been known.

Moreover, according to the AE detector of the above embodiment, in which the parameters are UP, RMS, FC, $G_{max}$, E, FM, WEFF or Q that can easily be calculated, a warning of destruction of the bearing 3 can therefore be easily calculated based on the signal of the AE sensor 5.

The AE detector of the first embodiment has the correlation parameter determining section 17 to determine the parameters that have a strong correlation by taking all the correlations of the various parameters. However, when the material subject to destruction detection is a specific material subject to destruction detection and two or more parameters that have a strong correlation formed based on AE generated from the specific material subject to destruction detection are previously known, it is not necessary to calculate the parameters that have a strong correlation by taking all the correlations of a plurality of parameters, and it is proper to calculate only two or more parameters that have the previously known strong correlation based on the signal from the AE sensor. Therefore, the correlation parameter determining section can be eliminated in this case.

Moreover, in the AE detector of the first embodiment, the parameter space to judge a warning of destruction of the bearing 3 is constituted of two dimensions (two dimensions constituted of FM and Q, two dimensions constituted of RMS and Q, and two dimensions constituted of RMS and FM). However, in the invention, the parameter space to judge a warning of destruction of the material subject to destruction detection may be constituted of three or more dimensions. For example, in the above example, a three-dimensional parameter space constituted of FM, Q and RMS may be adopted. In this case, it is needless to say that the first through third regions are three-dimensional spaces. Moreover, all the correlations of two parameters (two dimensions) are taken in the first embodiment. However, in the invention, the correlation parameter determining section may take all the correlations of three parameters (three dimensions) or four or more parameters (four or more dimensions).

Figure 7:
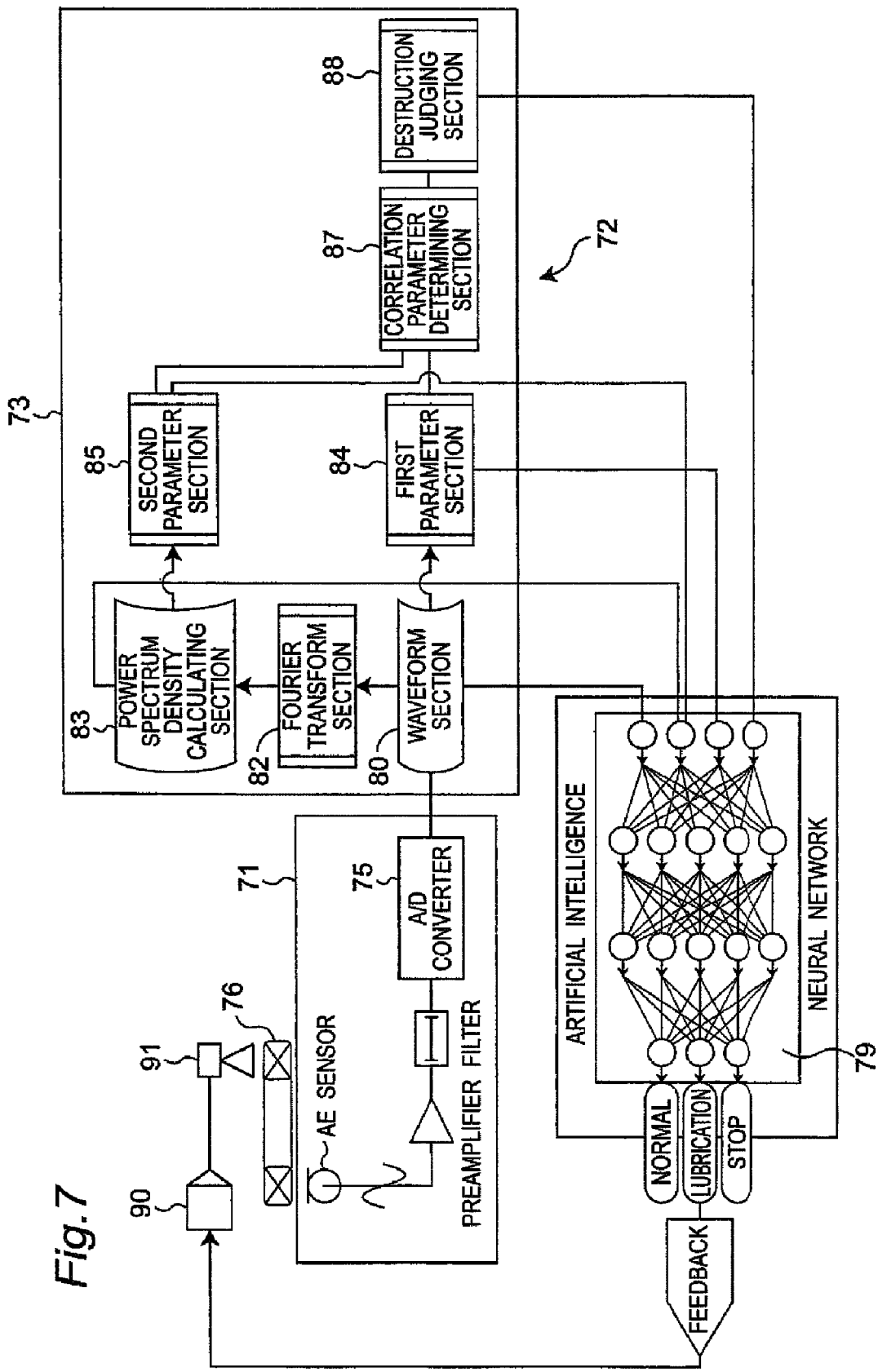
FIG. 7 is diagram showing the construction of a controller of the first embodiment of the invention.

FIG. 7 is a diagram showing the controller of the first embodiment of the invention.

The controller has the AE detector 72 of the second embodiment and a neural network 79. Upon receiving the output of the AE detector 72, the neural network 79 outputs a control signal to a pump controller 90.

With regard to the AE detector 72 of the second embodiment, no description is provided for the components, the operational effects and the modification examples common to those of the AE detector of the first embodiment, and only the construction and operational effects different from those of the AE detector of the first embodiment are described.

The AE detector of the second embodiment has an AE obtaining part 71 and a signal analyzing part 73. The AE obtaining part 71 has a construction identical to that of the AE obtaining part 1 of the first embodiment. Moreover, the signal analyzing part 73 has a waveform section 80 that receives a digital signal from an A/D converter 75 and displays the relation between time and the digital signal, a Fourier transform section 82 that receives a signal from the waveform section 80 and subjects the waveform displayed by the waveform section 80 to Fourier transform, a power spectrum density calculating section 83 that calculates a power spectrum density function by using a Fourier component calculated by performing the Fourier transform by the Fourier transform section 82, a first parameter section 84 that calculates various time-domain parameters based on the signal from the waveform section 80, and a second parameter section 85 that calculates various spectral parameters based on the signal from the power spectrum density calculating section 83. The first parameter section 84 and the second parameter section 85 constitute a calculating section.

The signal analyzing part 73 has a correlation parameter determining section 87 that receives a signal from the first parameter section 84 and a signal from the second parameter section 85 and performs a factor analysis, and a destruction judging section 88 that receives a signal from the correlation parameter determining section 87. The destruction judging section 88 performs a cluster analysis on parameters that exhibit a strong correlation determined by the correlation parameter determining section 87 upon receiving a signal from the correlation parameter determining section 87 and outputs a signal that represents the presence or absence of a warning of destruction of the bearing 76 or the destruction of the bearing 76 if possible. The destruction judging section 88 outputs the result of the cluster analysis also when the judgment of the presence or absence of a warning of destruction of the bearing 76 is impossible.

In the AE detector of the second embodiment, the waveform section 80 outputs a signal to the first parameter section 84 and outputs a signal also to the neural network 79. Moreover, the power spectrum density calculating section 83 outputs a signal to the second parameter section 85 and outputs a signal also to the neural network 79. Moreover, the first parameter section 84 and the second parameter section 85 output signals to the correlation parameter determining section 87 and output signals also to the neural network 79. Moreover, the destruction judging section 88 outputs a signal to the neural network 79.

The neural network 79 receives signals from the waveform section 80, the power spectrum density calculating section 83, the first parameter section 84, the second parameter section 85 and the destruction judging section 88 and outputs a signal that represents the presence or absence of a warning of destruction of the bearing 76 or the destruction of the bearing. In detail, when receiving a signal that represents the presence or absence of a warning of the bearing 76 or the destruction of the bearing 76 from the destruction judging section 88, the neural network 79 outputs a signal representing the fact that the bearing 76 is normal, a signal that represents a warning of destruction of bearing 76 (signal that represents supply of lubricant to the bearing 76) or a signal that represents the destruction of the bearing 76 (signal that represents stop of the operation of the machine in which the bearing 76 is installed) based on the signal. Moreover, the neural network 79 judges the presence or absence of a warning of the destruction of the bearing 76 or the destruction of the bearing 76 when the result of the cluster analysis is only received from the destruction judging section 88. Then, a signal that represents normality is outputted to the outside when there is no warning of destruction of the bearing 76, and a signal that represents supply of lubricant to the bearing 76 is outputted to the pump controller 90 when a warning of destruction of the bearing 76 is judged. Moreover, a pump 91 supplies lubricant to the bearing 76 upon receiving the signal that represents supply of lubricant to the bearing 76 from the pump controller 90. Moreover, the neural network 79 outputs a signal that represents stop of the operation of the machine in which the bearing 76 is installed to the outside upon judging that the bearing 76 is destroyed.

The neural network 79 has a knowledgeable database. The knowledgeable database receives signals from the waveform section 80, the power spectrum density calculating section 83, the first parameter section 84, the second parameter section 85 and the destruction judging section 88, collects information and knowledge and stores the same. The neural network 79 makes use of the knowledgeable database that have been digitized and stored and stores the information in an associative manner into the knowledgeable database.

That is, the neural network 79 stores the signals from the waveform section 80, the power spectrum density calculating section 83, the first parameter section 84, the second parameter section 85 and the destruction judging section 88 in a mutually combined state. The neural network 79 extracts one by the other combined with it, i.e., searches from part of the stored contents the stored contents that coincide with them.

In concrete, when it is judged that part of the input information is the information already stored in the knowledgeable database or the information that resembles the stored information, the neural network 79 regards the part of the input information as identical to the stored information and then outputs the information that represents the presence or absence of a warning of destruction of the bearing 76 or the information that represents the destruction of the bearing 76 combined with the stored information. In concrete, the neural network 79 judges the presence or absence of a warning of destruction of the bearing 76 or the destruction of the bearing 76 by using only the partial information of the information from the waveform section 80, the power spectrum density calculating section 83, the first parameter section 84, the second parameter section 85 and the destruction judging section 88 in such a case. It is noted that the signal analyzing part 73 is provided by software in the second embodiment. Moreover, as shown in FIG. 7, the controller of the first embodiment controls the pump 91 in a feedback manner to consistently maintain an optimal lubrication condition of the bearing 76.

According to the controller of the first embodiment, the more the AE detector 72 is used, the more the neural network 79 learns the relations between the signals from the waveform section 80, the power spectrum density calculating section 83, the first parameter section 84, the second parameter section 85 and the destruction judging section 88 and the presence or absence of a warning of destruction of the bearing 76 or the destruction of the bearing 76. The learned results can be reflected on the subsequent judgment of the neural network 79. Therefore, a warning of destruction of the bearing 76 can be judged more promptly and accurately as the AE detector 72 is used more and more.

Figure 8:
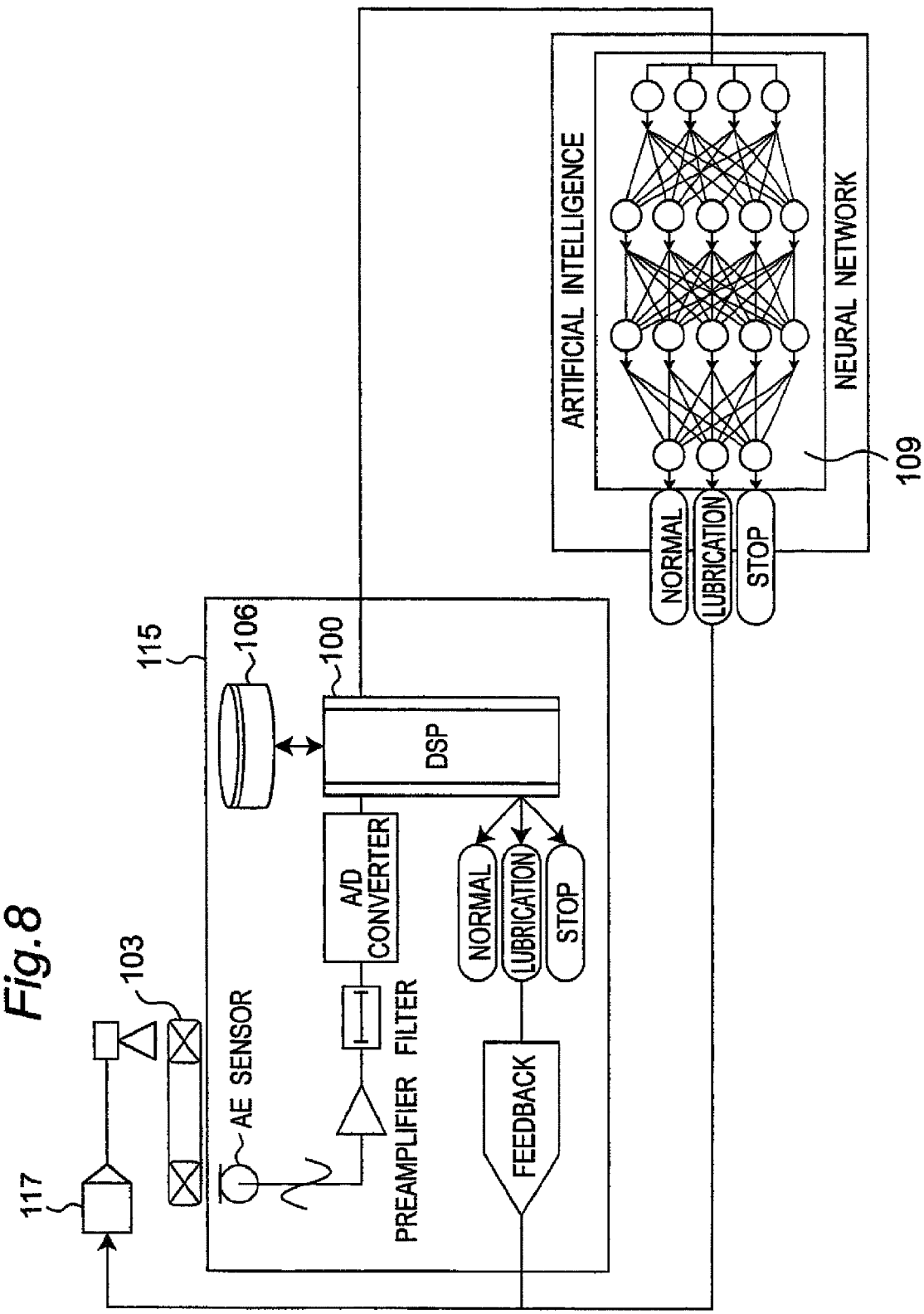
FIG. 8 is diagram showing the construction of a controller of a second embodiment of the invention.

FIG. 8 is a diagram showing the construction of the controller of the second embodiment of the invention.

The controller of the second embodiment has an AE detector 115 of a third embodiment and a neural network 109. The neural network 109 receives an output of the AE detector 115 and outputs a control signal to a pump controller 117.

With regard to the AE detector 115 of the third embodiment, no description is provided for the components, the operational effects and the modification examples common to those of the AE detectors of the first and second embodiments, and only the construction and operational effects different from those of the AE detector of the first and second embodiments are described.

The AE detector 115 of the third embodiment has a microprocessor (digital signal processor) 100 specializing in signal processing performed by the signal analyzing part of the AE detector of the first embodiment, and a destruction judging section (not shown) is built in the microprocessor 100. The microprocessor 100 exchanges information with a memory 106.

The microprocessor 100 judges the presence or absence of a warning of destruction of the bearing 103 or the destruction of the bearing 103 as one example of the material subject to destruction detection and outputs a signal that represents normality, a signal that represents lubrication or a signal that represents that the bearing 103 has been destroyed if possible. The neural network 109 receives a signal from the microprocessor 100. The neural network 109 judges the presence or absence of a warning of destruction or the destruction of the bearing 103 when the judgment of the presence or absence of a warning of destruction or the destruction of the bearing 103 is difficult in the microprocessor 100 and outputs a signal representing that the bearing 103 is normal, a signal that represents supply of lubricant to the bearing 103, or a signal that represents that the bearing 103 has been destroyed.

The neural network 109 receives a signal from the microprocessor 100 of the AE detector 115 of the third embodiment placed in a variety of places (locations). The neural network 109 is designed to grow as a knowledgeable database by data collection from the microprocessor 100 placed in each location. Each AE detector 115 of the third embodiment is installed in each location. A plurality of AE detectors 115 that output signals to the neural network 109 operate mutually independently. Moreover, the neural network 109 is located in a place separated from every location. The neural network 109 receives the signal from the microprocessor 100 located in each location by wires or wirelessly.

It is noted that the neural network 109 constitutes part of a center portion (not shown). The center portion has a control section and is able to remotely control the setting of the microprocessor 100 located in each location by a signal from the control section. Then, variables necessary for calculating the parameters, i.e., settings of a time width T and the like of the effective value RMS can freely be changed in the microprocessor 100 installed in each location.

In the controller of the second embodiment, one neural network 109 is shared by the plurality of AE detectors 115, and therefore, the growth rate of the knowledgeable database of the neural network 109 can be made remarkably rapid. Therefore, the speed of judging the presence or absence of a warning of destruction of the bearing 103 can be made remarkably rapid.

Although the materials subject to destruction detection are the bearings 3, 76 and 103 in the first through third embodiments, it is a matter of course that the material subject to destruction detection may be a machine such as a pulley, a generator turbine or a rotary shaft other than the bearing in the invention.

The invention claimed is:

1. An acoustic emission detector comprising:
an acoustic emission sensor configured to detect an acoustic emission;
a destruction judging section that judges that a material is subject to destruction when a predetermined number or more of points defined by at least two parameters calculated based on a signal from the acoustic emission sensor are located within a predetermined region of a parameter space in the parameter space defined by at least two parameters that are configured to be generated based on the signal from the acoustic emission sensor;
a calculating section that calculates a plurality of parameters based on the signal outputted from the acoustic emission sensor; and
a correlation parameter determining section that determines mutually correlated parameters among the plurality of parameters and that determines parameter combinations of which absolute values of correlation coefficients are not smaller than a predetermined value and which have a strong tendency of linearity, wherein
the destruction judging section judges that the material is subject to destruction when a predetermined number or more of points defined by mutually correlated parameters calculated based on the signal from the acoustic emission sensor are located within a predetermined region of the parameter space defined by the mutually correlated parameters in the parameter space defined by the mutually correlated parameters determined by the correlation parameter determining section.

2. The acoustic emission detector as claimed in claim 1, wherein
the parameter space comprises:
a first parameter space defined by at least two parameters; and
a second parameter space that is defined by at least two parameters and is different from the first parameter space.

3. The acoustic emission detector as claimed in claim 1, wherein
the at least two parameters are two or more parameters of UP, RMS, FC, Gmax, E, FM, WEFF and Q.

4. A controller comprising:
the acoustic emission detector claimed in claim 1; and
a neural network that receives at least an output of the acoustic emission detector and outputs a control signal.

* * * * *